United States Patent [19]

Meislitzer et al.

[11] Patent Number: 4,498,866
[45] Date of Patent: Feb. 12, 1985

[54] SAGGER FURNACE

[75] Inventors: Karl H. Meislitzer, Wiesbaden; Wigbert Hauner, Langen, both of Fed. Rep. of Germany

[73] Assignee: Dentsply Research & Development Corp., Milford, Del.

[21] Appl. No.: 462,916

[22] Filed: Feb. 1, 1983

[30] Foreign Application Priority Data

Feb. 18, 1982 [DE] Fed. Rep. of Germany ....... 3205729

[51] Int. Cl.$^3$ ............................ F27D 3/00; C21D 1/74
[52] U.S. Cl. .................................... 432/239; 266/250
[58] Field of Search ............... 432/239, 205, 206, 241; 266/250

[56] References Cited

U.S. PATENT DOCUMENTS

| | | |
|---|---|---|
| 569,911 | 10/1896 | Custer . |
| 657,202 | 9/1900 | McBrair . |
| 1,938,306 | 12/1933 | Webb ................................ 432/206 |
| 3,151,851 | 10/1964 | Negley ............................... 432/205 |
| 3,202,406 | 8/1965 | Tack .................................... 432/239 |
| 3,463,470 | 8/1969 | Green et al. ....................... 432/241 |
| 3,732,068 | 5/1973 | Larker ................................ 432/205 |
| 4,332,553 | 6/1982 | Earle et al. . |

FOREIGN PATENT DOCUMENTS 347572 2/1978 Austria .
2632846 2/1977 Fed. Rep. of Germany .

Primary Examiner—John J. Camby
Attorney, Agent, or Firm—Edward J. Hanson, Jr.; C. Hercus Just

[57] ABSTRACT

A sagger furnace especially adapted for the dental ceramic field. The furnace has a sagger platform and a top part that closes with the sagger platform to form a closed firing chamber. The upper part is powered by a positive drive but connected to the powering means by gravity force which allows the manual opening of the furnace at any time. Also provided is a method of firing dental ceramics.

9 Claims, 2 Drawing Figures

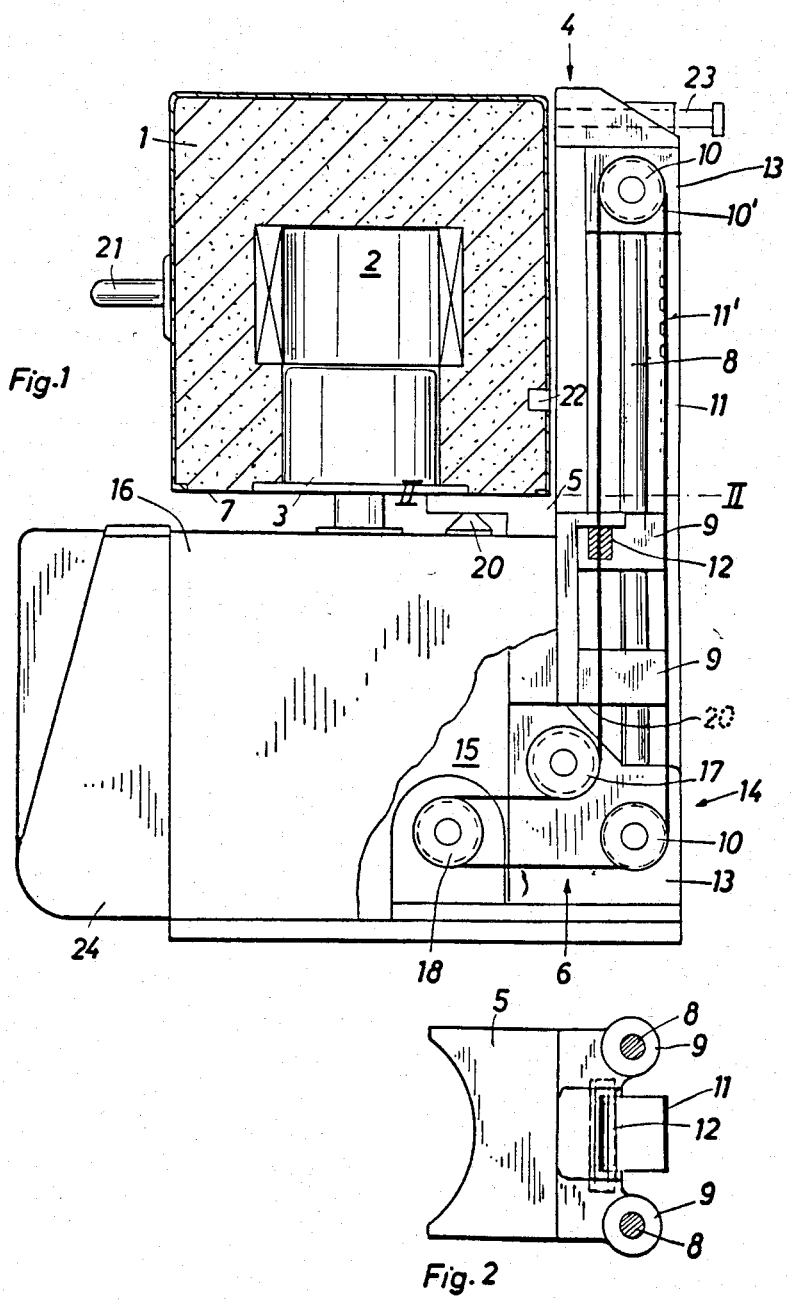

SAGGER FURNACE

BACKGROUND OF THE INVENTION

This invention relates to a sagger furnace and a method of saggering and especially in the dental ceramic field.

Furnaces of this general type are disclosed in DE-OS No. 26 32 846. Similar designs are represented by U.S. Pat. Nos. 657,202 and 569,911. These known furnaces have an upper part that includes a firing chamber that is connected to a stationary lower part by lateral joints and opens according to a set radius for loading the furnace and closes for the firing cycle as well as folds upward again on completion.

The furnace shown in DE-OS No. 26 32 846 has the cavity forming the firing chamber in the hinged upper part. The furnaces in the U.S. patents have the cavity forming the firing chamber in the upper and lower part.

These known types of openings and closings of the firing chamber do not provide uniform control over cooling the work.

It is, however, possible to provide more uniform control with the furnace shown in DE Pat. No. 347 572. The furnace shown in DE No. 347 572 moves the sagger platform upwards into a stationary upper part which contains the firing chamber and is open at the bottom. The lower part contains all of the electromechanical elements and display elements. In order to have the movable platform exposed for loading the complete top part has to be positioned at a sufficient height on adequately high columns. Furthermore, the required flexibility of the sagger platform with respect to stand security of the work entered is not advantageous. This furnace represents a bulky, high-built structure.

Accordingly, the invention is based on the need to provide a furnace that has selective and uniform cooling of the work without the disadvantages of prior teachings and with an arrangement of the required drive train that is uncomplicated and allows the opening and closing of the firing chamber independently of the drive train.

SUMMARY OF THE INVENTION

By an aspect of our invention a dental ceramic firing furnace is provided that has a stationary sagger platform, a firing chamber having an opening in the bottom thereof dimensioned for receiving the stationary sagger platform and means for lowering the firing chamber into receipt of the stationary sagger platform and raising the firing chamber from receipt of the stationary sagger platform and to expose the stationary sagger platform for charging and emptying the stationary sagger platform. Preferably the means for lowering and raising the firing chamber includes a tappet engaging the lower portion of the firing chamber and at least one guide element engaged with the tappet and a tappet shoulder engaging the tappet and powered to raise and lower the firing chamber.

A preferred guide element is a pair of spaced apart vertical rods with the tappet slidably bushed to them. The tappet preferably has an aperture therethrough through which a driving element passes and the tappet shoulder is larger in at least one dimension than the aperture and not able to pass through the aperture, thereby engaging the tappet.

By a further aspect of the present invention a method of firing dental ceramics is provided that includes placing a dental ceramic on a sagger platform, closing a firing chamber with the sagger platform and opening the firing chamber from the sagger platform while maintaining the sagger platform stationary. The firing chamber is closed by lowering the chamber vertically down over the sagger platform and opened by raising the firing chamber vertically up from the sagger platform. Preferably the firing chamber is lowered and raised by a powered means connection secured only by gravity, allowing a quick manual raising of the firing chamber in case of need without the necessity of disconnecting or overriding the powered means. The preferred is a non slipping positively driven means.

Preferably the firing chamber is provided with a vacuum after closing and the vacuum is released prior to opening the firing chamber.

By another aspect of the present invention a sagger furnace is provided that has a stationarily mounted sagger platform, a firing chamber having an opening in the bottom thereof dimensioned and aligned for receiving the stationarily mounted sagger platform and means for lowering the firing chamber vertically in alignment with the sagger platform to enclose the sagger platform and for raising the firing chamber from the sagger platform and to open the platform for loading and unloading. Preferably the means for lowering and raising the firing chamber includes a driving element engaged with the firing chamber in an engagement that can be disconnecting in response to manual raising of the firing chamber without requiring any specific disconnect action.

DRAWINGS

FIG. 1 is a partial sectional side plan view of a furnace of the present invention; and FIG. 2 is a partial top plan sectional view of the furnace taken at II—II of FIG. 1.

DESCRIPTION OF THE PREFERRED EMBODIMENT

Looking at FIG. 1 it will be seen that the furnace has a bottom housing 16, top part 1 with a downward opening firing chamber 2, and a stand 4.

A sagger platform 3 is installed stationarily on the housing 16 below and in alignment with the firing chamber 2. The position shown corresponds to the firing phase. The top part 1 of the furnace travels on the stand 4 which is not illustrated in detail. The driving elements for tappet or bracket mount 5, which is guided by means of ball bushings 9 on two guide rods 8 are, overall, designated 6.

Individually, in the preferred embodiment, the driving elements 6 consist of two bearing blocks 13, guide rollers 10, carried in the latter, with tooth system 10', a guide band 11 in the form of a tooth belt 11', and a motor drive 18 controllable from an electronic control 24 in a housing 16.

The tooth belt 11'— as illustrated — is right-angled at its lower end 14 and extends into the housing 16, through a return pulley 17 located on the lower bearing block 13 and the lower guide roller 10, running to the drive 18.

A tappet shoulder or lift lug 12 is attached firmly in fixed position at a certain location of the tooth belt 11', for engagement in effective connection with the tappet 5 carried on the guide rods 8, for the top part 1. In this regard, reference is made to FIG. 2.

Since only a force-based gravity effective connection exists between tappet 5 and top part 1, the top part 1 of the furnace can also be raised and lowered manually using the handle 21 without any problems.

In the case of a vacuum firing, the top part 1 seals with the sagger platform 3 in the known manner in addition to the sagger platform 3 serving as a lower stop, special stops 20 (also the surface of the lower bearing block 13) as indicated. The top part 1 may also be reasonably carried (slidably engaged with) on the guide rods 8 in obvious manner, not shown. The vacuum may be applied to and released from the closed furnace in known manner.

For the possible manual operation of the top part 1, there are provided on the stand 4 and on the top part 1 catching elements 22 and catching counter elements 23 in order to keep the top part 1 in the high opening position with respect to the sagger platform.

The top part 1 may be mounted on the stand 4 by means other than through guide rods 8 making it possible without any problems for all of the elements involved in the driving elements (5,8,9,10,10′,11,11′,12,17,18) to be designed as a complete assembly unit with a common bearing plate 19 which can be pushed into the housing 16 and to be fastened there and then unfastened and removed for servicing. The other means for connecting the top part 1 of the furnace to the stand could be through the addition of guide rods on the stand 4.

With respect to an exact parallel motion, the top part 1 is preferably also bedded on the guide rods 8, as described.

The tappet 5 may be — but does not have to be — connected firmly to the top part 1.

On lowering the top part 1 — regardless of whether there is a firm fixed or just a gravity force-based connection to tappet 5 — the top part follows the descending tappet shoulder or stop 12 with the tappet 5.

It is a principal feature of the present invention to arrange in and on the furnace housing all installations required for the operation of the furnace, the electronic control, switches, display instruments, vacuum installations, driving elements and the like, so that the top part, in regard to the stationary platform, can be lifted and lowered selectively and controlled via driving elements without firm connection to the driving elements and allowing the alternative manual lifting of the top part if required.

The top part (1) is carried, together with the downwards opening firing chamber (2), in alignment with the sagger platform (3) and vertically movable on stand (4). On the stand (4), there is a tappet (5) with forced guide, grabbing the lower side of the housing (7) of the top part (1) of the furnace from below, with driving elements (6). The driving elements (6) are provided with a tappet stop (12).

OPERATION

As may be seen in FIG. 1, the firing chamber 1 is closed with the sagger platform 3. To open the firing chamber, the motor drive 18 is rotated clockwise moving the tooth belt 11′ and powering the tappet shoulder 12 to lift tappet 5 and thereby, the firing chamber 1. The firing chamber 1 is lifted in alignment with the stationarily mounted sagger platform 3. The motor drive 18 is stopped to set the position of the firing chamber in its open position.

To lower the firing chamber or top part 1 and close the firing chamber with the sagger platform while maintaining the sagger platform stationary, the motor drive 18 is rotated counterclockwise, moving the tooth belt 11′ in the reverse direction and powering the tappet shoulder 12 downwardly. The tappet 5 follows the shoulder 12 down in response to gravity and the firing chamber 1 follows in like manner or if fixedly connected, the two members follow the shoulder 12 in response to gravity. The top part 1 is lowered vertically down over the sagger platform in alignment with it.

Because the firing chamber is only secured or connected to the tappet shoulder 12 directly or indirectly by a gravity connection, the top part 1 can be raised manually from its powered member by grabbing the handle 21 at anytime without the necessity of disconnecting or overriding the powered means.

It will be obvious to those skilled in the art that various changes and modifications may be made in the invention without departing from its true spirit and scope. It is, therefore, aimed in the appended claims to cover all such equivalent variations as fall within the true spirit and scope of the invention.

We claim:

1. A dental ceramic firing furnace comprising a base supporting a stationary sagger platform, vertical guide rod means on said base at one side of said plateform, a firing chamber having an opening in the bottom thereof dimensioned for receiving said stationary sagger platform and including guide bushings slidable upon said guide rod means, and power means on said base engageable with said guide bushings and operable for lowering said firing chamber to receive said stationary sagger platform and raising said firing chamber above said stationary sagger platform to expose said stationary sagger platform for charging and emptying said stationary sagger platform.

2. The dental ceramic firing furnace of claim 1 wherein said power means includes a tappet fixed to the lower portion of said firing chamber and a lift lug carried by a driven member engages said tappet to raise and lower said firing chamber.

3. The dental cermic firing furnace of claim 2 in which said driven member comprises an endless flexible member to which said lift lug is affixed and said member being guided for movement of said lug as aforesaid to raise and lower said firing chamber.

4. The dental ceramic firing furnace of claim 3 wherein said endless flexible member is an endless guided band driven by a reversing motor to raise and lower said firing chamber in response to the direction of drive of said motor.

5. The dental ceramic firing furnace of claim 4 wherein said endless guided band is a tooth belt.

6. The dental ceramic firing furnace of claim 5 wherein said endless guided band is guided by guide rollers and said guide rollers and said guide rod means are attached to said base.

7. The dental ceramic firing furnace of claim 6 further characterized by said base comprising a housing beneath said sagger platform and wherein said endless guided band at it lower end is led laterally into the inside of said housing by means of a return pulley adjacent said motor and is supported within said housing 8. The dental ceramic furnace of claim 1 including a handle on one side of said firing chamber and adapted to move said chamber manually.

9. The dental ceramic furnace of claim 1 further including a catching element on said firing chamber and a counter element mounted adjacent the upper end of said guide rod means and movalbe into engagement with said catching element to hold said firing chamber in raised position to expose said sagger platform.

* * * * *